United States Patent
Gottschalk et al.

(10) Patent No.: US 6,350,584 B1
(45) Date of Patent: Feb. 26, 2002

(54) **ELISA SERODIAGNOSIS OF PIG *PLEUROPNEUMONIAE* SEROTYPE 2**

(75) Inventors: Marcelo Gottschalk, St-Charles-sur-Richelieu; Daniel Dubreuil, Montréal; Réal Lallier, Ste-Hyacinthe, all of (CA)

(73) Assignee: Universite de Montreal, Montreal (CA)

(*) Notice: Subject to any disclaimer, the term of this patent is extended or adjusted under 35 U.S.C. 154(b) by 0 days.

(21) Appl. No.: 09/370,825

(22) Filed: Aug. 9, 1999

Related U.S. Application Data (63) Continuation-in-part of application No. 08/838,327, filed on Apr. 8, 1997, now abandoned.

(51) Int. Cl.[7] .................... C12Q 1/70; G01N 33/354; G01N 33/53; C12P 21/06; C12N 1/12
(52) U.S. Cl. .................... 435/7.92; 435/5; 435/7; 435/7.32; 435/7.9; 435/7.92; 435/69.3; 435/252.1; 436/518; 530/418
(58) Field of Search .................... 435/5, 7, 7.32, 435/7.9, 7.92, 69.3, 252.1; 436/518; 530/418

(56) References Cited

U.S. PATENT DOCUMENTS

| | | | |
|---|---|---|---|
| 4,182,856 A | | 1/1980 | Buckler et al. |
| 4,698,298 A | | 10/1987 | Dedieu et al. |
| 4,745,074 A | * | 5/1988 | Schreuer et al. ............ 436/518 |
| 4,774,177 A | * | 9/1988 | Marks ........................... 435/7 |
| 4,814,269 A | * | 3/1989 | Karpas ........................... 435/5 |
| 4,839,298 A | * | 6/1989 | Kay et al. .................... 436/175 |
| 4,954,630 A | | 9/1990 | Klein et al. |
| 5,013,646 A | * | 5/1991 | Woiszwillo ............... 435/7.92 |
| 5,156,948 A | * | 10/1992 | Christensen et al. ........... 435/5 |
| 5,304,645 A | | 4/1994 | Klein et al. |
| 5,648,227 A | * | 7/1997 | Basboll ..................... 435/7.32 |

FOREIGN PATENT DOCUMENTS

| | | |
|---|---|---|
| EP | 0875760 | 11/1998 |
| WO | WO 97/46883 | 12/1997 |

OTHER PUBLICATIONS

Altman et al., 1989, Carbohydrate Res, 191:295–30.
Altman et al., 1988, Biochem Cell Biol, 66:998–1004.
Benyon et al., 1991, Carbohydrates Res, 209:211–23.
Bosse et al., 1998, Can J Res, 54:320–5.

(List continued on next page.)

*Primary Examiner*—Jennifer Graser
*Assistant Examiner*—Ja-Na A. Hines
(74) *Attorney, Agent, or Firm*—Klauber & Jackson (57) ABSTRACT

The present invention relates to an ELISA diagnostic kit for the assay of *A. pleuropneumoniae* serotype 2 antibodies in the serum of pigs comprising in separate packaging, at least one of the following: a) a plate or solid support having bound thereto a purified lipopolysaccharide *A. pleuropneumoniae* serotype 2 antigen for a specific binding to anti-*A. pleuropneumoniae* serotype 2 antibodies present in the serum of pigs; b) serum from pigs experimentally inoculated with a strain of *A. pleuropneumoniae* serotype 2 to serve as a positive control; c) pig serum from *A. pleuropneumoniae* free herd to serve as a negative control; and d) a detectably labeled conjugate which bind to pigs antibodies bound to the plate of a).

19 Claims, 1 Drawing Sheet

BL = BLANKS
CP = POSITIVE CONTROL
CN = NEGATIVE CONTROL
S1 TO S40 = SERUM TO BE ANALYZED

OTHER PUBLICATIONS

Bosse et al., 1990, Can J Vet Res, 54:427–31.
Gottschalk et al., 1994, Vet Microbiol, 42: 91–104
Goutte et al., 1986, Int Pig Vet Soc Proc, 9:258.
Bosse et al. 1989. Capsular Polysaccharide Antigens for Detection of Serotype–specific Antibodies to *Actinobacillus pleuropneumoniae* Can J. Vet. Res. 54:320–325, 1989.*
Bosse et al. 1990. Serodiagnosis of *Pleuropneumonia* Using Enzyme–linked Immunosorbent Assay with capsular Polysaccharide Antigens of *Actinobacillus pleuropneumoniae* Serotypes 1,2,5 and 7. Vet. Res. 54:427–431, 1990.*
Inzana et al. 1987. Serotype Specifity and Immunogenicity of the Capsular Polymer of *Haemophilus pleuropneumoniaae* Serotype 5. Infection and Immunity. 55(7): 1580–1587, 1987.*
Trottier et al. 1992. optimization and Standardization of an Enzyme–Linked Immunosorbent Assay Protocol for Serodiagnosis of *Actinobacillus pleuropneumoniae* Serotype 5. J. of Clin. Micro. 30(1):46–53, 1992.*
Nielsen et al. 1991. Blocking ELISA for Detection of Antibodies to *Actinobacillus–pleuropneumoniae* serotype 2. J. Clin. Microbio. 29(4):794–797, 1991.*
Nielsen et al. 1993. Antibodies against *Actinobacillus pleuroopneumoniae* serotype 2 in mucosal secretions and sera of infected pigs as demonstrated by an enzyme–linked immunosorbent assay. Res. Vet. Sci. 54(1):57–62, 1993.*
Nielson et al. 1995. Detection of antibodies against *Actinobacillus pleuropneumoniae,*serotype 2 in porcine colostrum using a blocking ELISA specific for serotype 2. Vet. Microbio. 43(4):277–281, 1995.*
Gray et al., 1979, J Immun Methods, 28:187–92.
Inzana et al., 1987, Infection and Immunity, 55:1580–7.
Mittal eta l., 1984, Am J Vet Res, 45:715–9.
Nadeau et al, 1991, Bulletin Epidemiologiique, 2:4–5.
Nielsen et al., 1991, J Clin Microbio. 29:794–7.
Nielsen et al., 1993, Res Vet Sci 54:57–62.
Nielsen et al., 1995, Vet Microbio, 43:277–81.
Perry et al., 1990, Sero Immunol Infect Dis, 4:299–308.
Trottier et al., 1992, J Clin Microbiol, 30:46–53.

* cited by examiner

BL = BLANKS
CP = POSITIVE CONTROL
CN = NEGATIVE CONTROL
S1 TO S40 = SERUM TO BE ANALYZED

FIG_1

ELISA SERODIAGNOSIS OF PIG *PLEUROPNEUMONIAE* SEROTYPE 2

RELATED APPLICATION

This application is a continuation-in-part of application Ser. No. 08/838,327 filed on Apr. 8, 1997 now abandoned, which is hereby incorporated by reference in its entirety.

BACKGROUND OF THE INVENTION (a) Field of the Invention

The invention relates to kits for the accurate, rapid and sensitive assay of *A. pleuropneumoniae* serotype 2 antibodies in pig serum for swine pleuropneumonia serodiagnosis.

(b) Description of Prior Art

*Actinobacillus pleuropneumoniae* is known as one of the most pathogenic agents of the respiratory tract of swine. Swine pleuropneumonia is still an important problem in large swine operations, causing serious economic losses in this industry. Since the presence of *A. pleuropneumoniae* is often unnoticed in chronically infected herds, the identification of carrier animals is a main concern. Following a stressful situation, several clinically fatal cases may arise in a given herd. Infection in swine can be fatal but animals surviving the infection frequently become carriers. Detection of chronically infected carriers is crucial since those animals act as reservoirs of infection. Since the infection is often unnoticed, serology becomes a useful tool for the detection of chronic infection. Several studies indicate that it is possible to control or eliminate the infection in certain herds based on the serological results.

Various serological assays for *A. pleuropneumoniae* have been described. Among others, the complement fixation test (CFT), the enzyme-linked immunosorbent assay (ELISA); (Goyette G. et al., 1986, *Int. Pig. Vet. Soc. Proc.*, 9:258) and the 2-mercapto-ethanol tube agglutination test (Mittal, K. et al., 1984, *Am.J. Vet.Res.*, 45:715–719) have been used. Out of the different assays, the ELISA is often the most useful since it is faster and easier to perform. On the other hand, up to now, the results obtained suggested the use of a more purified antigenic preparation in order to improve the specificity of the test.

A saline extract of boiled-formalinized whole cells of *A. pleuropneumoniae* (also called crude extract) is presently used, in some laboratories, as the antigen for ELISA serodiagnosis (Goyette G. et al., 1986, *Int. Pig. Vet. Soc. Proc.*, 9:258). Standardization of the assay is complicated as variations are noticed between extracts.

Using different antigen preparations, cross-reactions among serotypes and with other bacterial species were also reported (Bossé, J. et al., 1990, *Can. J. Vet. Res.*, 54:427–431). Although the capsular polysaccharide (CPS) of *A. pleuropneumoniae* has been shown to be responsible for serotype specificity (Inzana, T. and Mathison, T., 1987, *Infect. Immun.*, 55:1580–1587), the difficulty of obtaining pure CPS in large quantity precludes its utilization for serodiagnostic purposes. The CPS were very unstable and were fixed with difficulty to the walls of the polystyrene plate used in the ELISA assay (Perry, B. et al., 1990, *Sero. Immunol. Infect. Dis.*, 4:299–308).

Serology, which is used to identify animals that have developed an immune response to specific pathogens, is an important tool in disease management and prevention of *A. pleuropneumoniae* infection in pigs. The importance of serological testing is further emphasized by the lack of a vaccine that reliably prevents infection.

The use of antibiotics is mainly useful to control the mortality, but it has no real benefit on pigs with chronic pleuropneumonia. Treated animals often continue to carry the organism and can be a source of infection for other animals. In addition, an increasing number of strains resistant to different antimicrobials has been observed in the last years in Quebec (Nadeau, M. and Higgins, R., 1991, *Bulletin épidémiologique*, 2:4–5).

The demand of pigs from *A. pleuropneumoniae* sero-negative herds is increasing, especially from producers whose herds have experienced acute outbreaks of the disease and who have decided to "eradicate" *A. pleuropneumoniae*, buying only sero-negative animals (coming from sero-negative herds) for the replacement. A successful eradication program depends mostly on the accuracy and reliability of the serological tests used to identify *A. pleuropneumoniae* infected pigs. Never-theless, interpretation of serology should be done cautiously. A test that is not sensitive will not detect all infected herds or animals (false negative results) and one that is not specific will erroneously condemn some non-infected animals (false positive results).

The antigenic specificity of *A. pleuropneumoniae* appears to be linked, at least partly, to the capsular polysaccharides (Altman et al., 1988, Biochem. Cell. Biol. 66:998–1004; Benyon et al., 1991, Carbohydrate Res., 209:211–223; Bosse et al., 1990a, Can. J. Res. 54:320–325, and 1990b, Can. J. Vet. Res. 54:427–431) or, according to other authors, to the smooth lipolysaccharides (Altman et al., 1989, Carbohydrate Res. 191:295–303; Benyon et al., 1991, Carbohydrate Res. 209:225–238). However, these capsular polysaccharides turn out to be very unstable and are difficult to attach to the polystyrene surfaces of the plates used for the ELISA (Perry et al., 1990, Immunother. Infect. Dis. 4:299–308; Gray B. M., 1979, J. Immun. Methods, 28:187–192).

There are some cross-reactions among serotypes; for example: serotypes 3, 6 and 8, serotypes 1, 9 and 11, and serotypes 7 and 4. It is not possible, so far, to differentiate these serotypes serologically. Most of these cross-reactions are due to the presence of common epitopes at the lipopolysaccharide (LPS) level. In addition, other cross-reactions, which are not found in serotyping, could be observed in serological analysis of chronically infected animals that are continuously challenged with the microorganism. These cross-reactions are usually associated with outer membrane proteins (cell wall proteins, iron-repressible proteins, etc.) and rough lipopolysaccharides. However, it is important to remember that one herd, and even one animal, might be infected with several serotypes simultaneously. In this case, the detected antibodies against different serotypes are probably not cross-reactions, but homologous and specific reactions. This is one of the most important problem to be solved by the use of specific and sensitive serological tests in accordance with the present invention.

Healthy carrier pigs may be responsible for the transmission of the disease. The absence of clinical signs and/or lesions at the slaughter-house does not implicate necessarily the absence of the infection.

Following infection, antibodies can usually be detected in 10–15 days. Some animals will remain serologically positive for a few months, but most will be positive for a long period of time; once more, it will depend on the test used.

The proportion of seropositive sows as well as their titers tended to decrease with age.

Isolation of *A. pleuropneumoniae* from apparently healthy carrier pigs is difficult; it probably should be used as a complement to the serology in conflictive cases.

The development of better serological tests is a necessity because the infection still has an economic impact on the swine industry and the current vaccines are not effective.

To date, there exist no stable kit for the effective serodiagnosis of pig pleuropneumonia in the field.

It would be highly desirable to be provided with a kit for readily determining the presence of antibodies against *A. pleuropneumoniae* serotype 2 in a serum sample.

It would be highly desirable to be provided with such ELISA diagnostic kit for *A. pleuropneumoniae* which could be used for *A. pleuropneumoniae* serodiagnosis while remaining in the field.

SUMMARY OF THE INVENTION

One aim of the present invention is to provide a kit for the accurate, rapid and sensitive assay of antibodies against *A. pleuropneumoniae* serotype 2 in a sample.

Another aim of the present invention is to provide an ELISA diagnostic kit for *A. pleuropneumoniae* to be used for *A. pleuropneumoniae* serodiagnosis while remaining in the field. The novelty and originality of the ELISA diagnostic kit of the present invention resides in the particular combination of a novel purification method of the antigen to be used and a novel sensitization and stabilization methods of the plates of the kit.

The kits of the present invention differs from the ELISA method of the prior art for the determination of *A. pleuropneumoniae* antibodies. In the prior art method, the antigen is fixed to the plates in a PBS buffer and the plates are immediately used after the antigen fixation is completed. The prior art method may include a computerized reading protocol for the determination of the antibodies in the samples as described by Trottier, Y. L. et al. (1992, *J. Clin. Microbiol.*, 30:46–53). The kits of the present invention mainly differ in that the antigen is purified using a higher concentration of phenol,the antigen fixation procedure is different, and the fixed antigen is stored in a horseradish peroxidase (HRP) conjugate stabilizing solution (sold by Calbiochem-Novabiochem Corporation, La Jolla, Calif. 92039, U.S.A., catalogue #516534, containing phosphate buffered saline pH 7.2, BSA, 0.1% thimerosal and caprylic acid).

Thus, the purified antigen is resuspended in a PBS-EDTA buffer which is then added to each well of the plate. After an 18 hour incubation, horseradish peroxidase (HRP) conjugate stabilizing solution is added to each well. The antibodies in the samples can be determined visually by adding a chromogen, preferably 3,3',5,5'-tetramethylbenzidine, e.g. TMBlue™ (Biovest Inc., Massachusetts, USA)(see U.S. Pat. No. 5,013,646, issued May 7, 1991). The kits of the present invention, when compared to the prior art ELISA method, demonstrate a relative sensitivity and a relative specificity of 100%.

In accordance with another embodiment of the present invention there is provided an ELISA diagnostic kit for the assay of *A. pleuropneumoniae* serotype 2 antibodies in the serum of pigs comprising in separate packaging, at least one of the following:

a) a plate or solid support having bound thereto a purified lipopolysaccharide *A. pleuropneumoniae* serotype 2 antigen for a specific binding to anti-*A. pleuropneumoniae* serotype 2 antibodies present in the serum of pigs;

b) serum from pigs experimentally inoculated with a strain of *A. pleuropneumoniae* serotype 2 to serve as a positive control;

c) pig serum from a specific pathogen free herd to serve as a negative control; and d) a detectably labeled conjugate which binds to the pig antibodies bound to the plate of a).

The antigen of step a) when bound to a solid support can be stabilized by storing it at 4° C. in the HRP conjugate stabilizing solution which keeps the bound antigen stable for at least 25 weeks.

The ELISA diagnostic kits of the present invention may further comprise the following:

e) a substrate which allows the visualization of the detectably labeled conjugate.

In accordance with another embodiment of the present invention there is provided a method for the preparation of the kit, which comprises the steps of:

a) purifying lipopolysaccharide *A. pleuropneumoniae* serotype 2 antigen by phenol extraction and centrifugation of said antigen bacterial crude extract;

b) fixing the antigen of step a) to a solid support and stabilizing said fixed antigen;

c) immunizing mammals with a strain of *A. pleuropneumoniae* serotype 2 and collecting serum to serve as positive control sera; and d) collecting sera from *A. pleuropneumoniae* free herds to serve as negative control sera.

The stabilizing of the solution of step b)may be achieved by storing it in an HRP conjugate stabilizing solution at 4° C., which keeps the bound antigen stable for at least 25 weeks. In a particular embodiment, the HRP conjugate stabilizing solution contains phosphate buffered saline pH 7.2, 20 mg/ml BSA, 0.1% thimerosal and a saturating amount of caprylic acid.

DETAILED DESCRIPTION OF THE INVENTION

The kits of the present invention are novel in that they allow for a simple and fast testing in the field where the animals are. These kits are sufficiently stable that they have a shelf life of at least 3 and one half months. The antigen was purified according to a novel procedure which allows for an increased sensitivity.

Heretofore, once an antigen was bound to the plate, the antigen was unstable. In contrast, the bound antigen stabilized by the HRP conjugate stabilizing solution (sold by Calbiochem-Novabiochem Corporation, La Jolla, Calif. 92039, U.S.A., catalogue #516534, i.e. phosphate buffered saline pH 7.2, containing BSA, 0.1% thimerosal and caprylic acid)in accordance with the present invention, is stable for a long time. In fact, the antigen will remain stable for at least 25 weeks or until use.

The kits of the present invention are based essentially on the particular combination of a novel method of purification of lipopolysaccharide antigen from a reference strain of *A. pleuropneumoniae* serotype 2 antigen and a novel coating and stabilization of the antigen on the surface of the plate. The kit in accordance with the present invention is very specific, sensitive and stable. The test in accordance with the kit of the present invention consists in the determination of the presence or absence of anti-*A. pleuropneumoniae* antibodies in the serum of pigs for the serodiagnosis of *A. pleuropneumoniae* serotype 2.

The test essentially consists in the following steps:

a) A plate of 96 wells sensitized with the specific antigen of *A. pleuropneumoniae* serotype 2 is washed with a PBS-TWEEN™-20 buffer solution (TWEEN™-20: ICI Americas Inc., Delaware, USA).

b) A serum sample of each pig from the tested herds is distributed in two sensitized wells of step a). During this first incubation, the anti-*A. pleuropneumoniae* serotype 2 antibodies, if present in the sera, will bind to the antigen attached to the plate or solid phase bound.

c) The plate is washed to remove from the wells any unbound material. A peroxidase-anti-IgG conjugate is added to each well, preferably obtained from Jackson Immuno Research Laboratories (catalogue #114-035-003). This conjugate binds to any IgG which would have bound to the antigen attached to the plate in step b). If the pig serum did not contain any anti-*A. pleuropneumoniae* serotype 2 antibodies, the conjugate will remain free or in suspension and will be eliminated during this washing step.

d) The presence of immobilized peroxidase within the bound conjugate is revealed by the addition of a chromogen substrate 3,3',5,5'-tetramethylbenzidine (TMBLue™) (sold by Transgenic Science Inc., Milford' Mass. 01757, U.S.A., catalogue #TM-102). If the conjugate is present, there will be an oxidation reaction and a blue color will appear.

The preferred kit of the present invention comprises the following items:

1—Five 96-well plates (Nunc™, sold by Gibco, Burlington, Ontario, Canada, L7P 1A1) sensitized and stabilized with the purified antigen in accordance with the present invention.

2—Positive control; five vials containing each 0.1 ml of lyophilized serum from pigs experimentally inoculated with a strain of *A. pleuropneumoniae* serotype 2.

3—Negative control; five vials containing each 0.1 ml of lyophilized pig serum from a specific pathogen free herd.

4—Weak positive control; five vials containing each 0.1 ml of lyophilized serum from pigs experimentally inoculated with a strain of *A. pleuropneumoniae* serotype 2.

5—Conjugate; five vials of pig anti-IgG immunoglobulins coupled to peroxidase. Each vial contains 1.2 ml of conjugate stabilized with HRP (Calbiochem Corporation, Canada, #516534).

6—3,3',5,5'-tetramethylbenzidine (TMBLue™); five vials containing each 12 ml of 3,3',5,5'-tetramethylbenzidine (TMBLue™).

Figure 1:
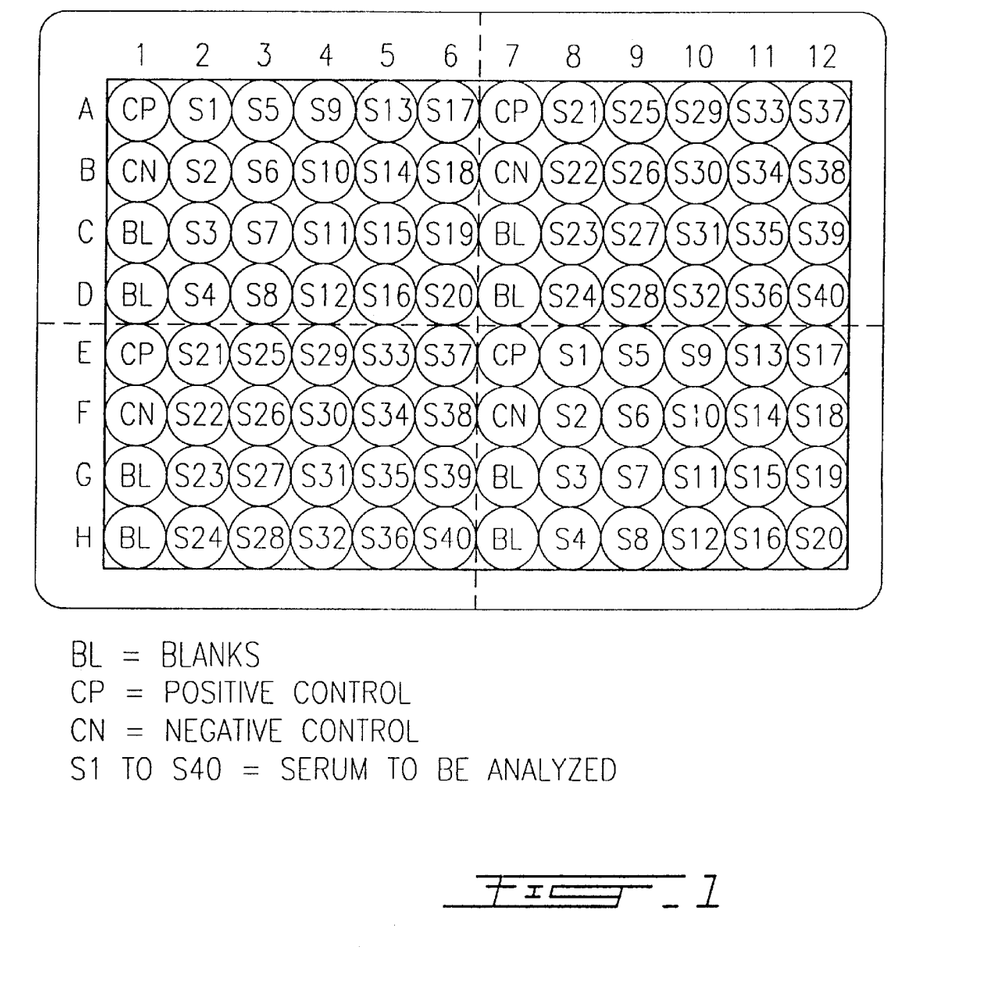
FIG. 1 illustrates the layout of the plate of the preferred kit of the present invention.

FIG. 1 illustrates the layout of the plate of the preferred kit of the present invention, where 40 different sera are analyzed. The wells are identified as follows:
BL=Blanks, PBS-Tween™-20 buffer solution (4 wells)
CP=Positive control, item #2 above (4 wells)
CN=Negative control, item #3 above (4 wells)
CPFA=Weak positive control, item #4 above (4 wells)
S1 to S40=serum to be analyzed, 2 wells for each serum.

Preparation of the PBS-Tween™-20 Buffer Solution
Add the following to 3 L of distilled water,
52.59 g of sodium chloride;
1.47 g of monobasic sodium phosphate;
7.02 g dibasic sodium phosphate;
1.5 ml of Tween™-20.

Mix well until a complete dissolution is achieved. Verify the pH, which should be about 7.30±0.05, if different adjust the pH using dibasic sodium phosphate. This solution has a shelf life of 1 week when kept at 4° C. The buffer solution should always be brought to room temperature before being used in the test.

Bacterial Strain
The strain of *A. pleuropneumoniae* serotype 2, referred to as strain ATCC 27089, was used for the antigen production (Altman et al., 1987, Biochem. Cell Biol., 65:414–422). The strain was kept lyophilized.

Bacterial Culture
The content of a vial was resuspended in one ml of PPLO (Difco Laboratories, Detroit, Mich.) liquid medium and inoculated to exhaustion on a PPLO agar plate. The plate was incubated aerobically for 24 hours at 37° C.

A few colonies were resuspended in 5 ml of PPLO liquid medium. PPLO plates were inoculated at confluence with a sterile swab, these plates were then incubated 6 hours at 37° C. After the incubation, the bacterial growth was harvested by adding 3.0 ml of phosphate-buffered saline (PBS, pH 7.4) (Oxoid Ltd., Basingstoke, England) containing 0.5% (vol/vol) of formaldehyde (Fisher Scientific, Fair Lawn, N.J.) to each gel plates.

Antigen Purification
The bacterial suspension obtained was placed in a sterile bottle and was allowed to stand overnight at 4° C. The optical density was adjusted to 5.0 with a solution of PBS-0.5% formaldehyde. The suspensions were separated in sterile screw cap vials and boiled 60 min. Then the suspensions were centrifuged at 12,000×g for 30–40 min., 4° C. The supernatants were collected and filtered on a 0.22 μm pore size filter (Millipore Corp., Bedford, Mass.).

The antigen was purified according to the following procedure.

Preparing the phenol solution by mixing 90 g of phenol crystals with 100 ml of distilled water.

Mixing an equal volume of the phenol solution with an equal volume of the crude extract in Corex™ tubes, mixing by inversion and let stands for 30 min. at room temperature.

Centrifuged at 12,000×g, 4° C. for 30 min.

After the first centrifugation, two phases were obtained with an interface of insoluble material. The phenol phase was collected with a Pasteur™ pipette and the volume was measured in a graduated cylinder.

Mixing an equal volume of the phenol phase (first extraction) with an equal volume of the water phase in COREX™ tubes, mixing by inversion and let stands for 30 min. at room temperature.

Centrifuged at 12,000×g, 4° C. for 30 min.

The phenol phase was collected and the volume was measured in a graduated cylinder.

Mixing an equal volume of the phenol phase (second extraction) with an equal volume of the water phase in Corex™0 tubes, mixing by inversion and let stands for 30 min. at room temperature.

During this period, prepare the dialysis membrane by soaking in distilled water for a sufficient period of time.

Centrifuged at 12,000×g, 4° C. for 30 min.

The aqueous phase was collected and the volume was measured in a graduated cylinder.

The phenol phase (third extraction) was dialyzed against 3×12 L of distilled water to remove traces of phenol, do not dialyze for more than 24 hours.

Antisera—Negative Control
Sera from several pigs were obtained at the slaughter from a specific pathogen free herd; the sera were mixed and thimerosal (sold by Sigma, St-Louis, Mo. 14508, U.S.A., catalogue #T-5125) was added to obtain a final concentration of 0.01%. No history of *A. pleuropneumoniae* was ever reported for this herd since at least four years. The sera were tested using the ELISA technique against all the *A. pleuropneumonia* serotypes by the pleuropneumonia laboratory of the Veterinary Medicine Faculty of University of Montreal.

Antisera—Positive Control
The strain *A. pleuropneumoniae* serotype 2 (strain ATCC 27089) was used for the bacterial production. The content of a vial was resuspended in one ml of PPLO (Difco Laboratories, Detroit, Mich.) liquid medium and inoculated to exhaustion on two PPLO agar plates. The plates were incubated aerobically for 18 hours at 37° C.

The bacterial production for the immunization of pigs was effected according to the following procedure.

Collecting a few colonies isolated with a sterile swab and resuspending them in a PPLO broth.

5 PPLO agar plates were inoculated at confluence with the broth and sterile swabs. One Mueller-Hinton agar plate was inoculated with the remaining broth to serve as a negative control. One PPLO agar plate was inoculated to exhaustion.

These plates were then incubated 18 hours at 37° C. One plate is used for serotyping.

After the incubation, harvesting the bacterial growth by adding 3.0 ml of PBS-0.5% formaldehyde to each plate, and mixed with a hockey stick made of sterile Pasteur™ pipette and recovering the suspension with a pipette.

The bacterial suspension obtained was placed in a sterile bottle, mixed well and incubated 18 hours at room temperature.

The optical density was read at 540 nm and adjusted to 1.0 with a solution of PBS-0.5% formaldehyde.

The solution was kept at 4° C. until usage or for a maximum of one week.

For the immunization, four five-week old piglets were obtained from a specific pathogen free herd. No history of *A. pleuropneumoniae* was ever reported for this herd for at least four years and no pulmonary lesions were observed at the slaughter. At their arrival, the general state of health of the piglets is verified. The piglets are fed on demand with introductory fattening food for pigs (15/30 CO-OP). After a few days of adaptation, a blood sample is taken from each animal. The sera were tested using the ELISA technique against all the *A. pleuropneumoniae* serotypes by the pleuropneumonia laboratory of the Veterinary Medicine Faculty of University of Montreal. The sera were negative for all serotypes.

The pigs were immunized intravenously with 5 ml of the bacterial suspension every three weeks and this until the ELISA titer gives a value superior or equal to 1.0. The pigs were bled and the serum of each animal was mixed together.
ELISA For evaluating the efficiency and reliability of the kits of the present invention, two methods of ELISA were used. In the first method, the plates are used immediately after sensitization, the incubation period are of one hour and ABTS (2,2'-azino-bis(3-ethylbenzthiazoline)-6-sulfonic acid) is used as a chromogen. In the second method, the plates are treated with HRP conjugate stabilizing solution after sensitization, the incubation period is 15 min. and 3,3',5,5'-tetramethylbenzidine, (TMBLue™) is used as a chromogen.

The ELISA consists in:
1-sensitization of the plates

Diluting in 1.5 ml of antigen in 73.5 ml of PBS-EDTA buffer, pH 7.3.

Add 100 µl of antigen to each well.

Seal the plate with an acetate sheet.

Incubate overnight at 4° C.

For the evaluation of the kit, for the stability assays as well as for the visual assays, the plates are treated with HRP conjugate stabilizing solution (sold by Calbiochem-Novabiochem Corporation, La Jolla, Calif. 92039, U.S.A., catalogue #516534, i.e., phosphate buffered saline pH 7.2, containing BSA, 0.1% thimerosal and caprylic acid). The content of the wells are emptied and 100 µl of HRP conjugate stabilizing solution is added to each well. The plates containing the HRP conjugate stabilizing solution are kept at 4° C. until needed.

2-washing of the sensitized plates

Recovering the plate and emptying its content.

Filling each well with PBS-TWEEN™-20 buffer.

Emptying the plate content.

Repeat these steps four times.

Shake off 2–3 times on an absorbing paper to remove any washing solution excess.

3-sera preparation

The sera are diluted 1/200 in PBS-TWEEN™-20 buffer and distributed in the amount of 100 µl to each well.

Gently shake the plate to ensure the distribution of the samples at the bottom of the wells. Cover the plate with an acetate sheet.

Let the plate stand for one hour at room temperature for ELISA using ABTS or for 15 min. between 18° C. and 22° C. for ELISA using 3,3',5,5'-tetramethylbenzidine (TMBLue™).

4-washing of the plate to remove unbound antibodies

Recovering the plate and emptying its content.

Filling each well with PBS-TWEEN™-20 buffer.

Emptying the plate content.

Repeat these steps four times.

Shake off 2–3 times on an absorbing paper to remove any washing solution excess.

5-distribution of conjugate

The conjugate consists in horseradish peroxidase-labeled immunoglobulin G fraction of rabbit antiserum raised against porcine IgG (Jackson Immuno Research Laboratories Inc., catalogue #114-035-003). The conjugate is used at a final dilution of 1/6000. The conjugate is distributed in the amount of 100 µl to each well of the plate.

Gently shake the plate to ensure the distribution of the samples at the bottom of the wells. Cover the plate with an acetate sheet.

Let the plate stand at room temperature for one hour for ELISA using ABTS 2,2'-azino-bis(3-ethylbenzthiazoline)-6-sulfonic acid or for 15 min. for ELISA using TMBLue™.

6-washing of the plate to remove unbound conjugate

Recovering the plate and emptying its content.

Filling each well with PBS-Tween™-20 buffer.

Emptying the plate content.

Repeat these steps two times.

Shake off 2–3 times on an absorbing paper to remove any washing solution excess.

ELISA using ABTS

This was used only to validate the kit of the present invention or to get a spectrophotometer value.

7a-preparation and distribution of chromogen

The reaction was visualized using 3% $H_2O_2$ and 40 mM ABTS (2,2-azino-bis(3-ethylbenzthia-zoline-6-sulfonic acid) (Sigma Chemical) in 50 mM citrate solution (pH 5.0). Add 100 µl of this citrate-ABTS solution to each well of the plate.

Gently shake the plate to ensure the distribution of the samples at the bottom of the wells.

Let the plate stand for 30 min. at room temperature (between 18° C. and 22° C.).

8a—reading and results interpretation

The optical density was read at 414 nm using an automated plate reader (MR5000™, Dynatech Laboratories Inc.).

The results were calculated according to the following procedure.

1-The values of the eight wells BL (blank) were verified:
A value inferior to 0.08 indicates a valid test, continue the reading.
A value superior to 0.08 indicates an invalid test, repeat the test with a new kit or contact the kit manufacturer.

2-The mean values of the negative and positive controls are calculated as follows (see FIG. 1 for identification of wells):

Positive control=((A1+E1+A7+E7)/4)−BL mean
Negative control=((B1+F1+B7+F7)/4)−BL mean ELISA using TMBLue™ in accordance with the present invention 7b—preparation and distribution of chromogen Add 100 µl of 3,3',5,5'-tetramethylbenzidine (TMBLue™) to each well of the plate.

Gently shake the plate to ensure the distribution of the samples at the bottom of the wells.

Let the plate stand for 5 to 15 min. at room temperature (between 18° C. and 22° C.).

8b—reading and results interpretation

The visual reading was effected without any reading instruments as follows:

The results were calculated according to the following procedure.

1-The color of the eight wells BL (blanks) and of the negative controls is verified; it should be colorless.
2-The color of the positive controls is verified; it should be dark blue.
3-The color of the CPFA (weak positive control) is verified; it should be light blue.
4-The answer of each sample should be quantified as follows:
0=colorless well or slightly bluish
1+=well of a light blue color
2+=well of a blue color
3+=well of a dark blue color
4+=well of a dark blue color The reading with a spectrophotometer was effected and calculated as described in section 8a above. The positive control should present an optical density $\geq 1.0$ to accept the plate

RESULTS

Reproducibility of the Antigen Attachment

The aim of this test series consists in verifying the reproducibility of the antigen bounding at the bottom of the wells of the plate. The variation in the antigen attachment between the wells of a same plate was determined. Each of the 96 wells of each three plates was sensitized with 1/50 dilution of *A. pleuropneumoniae* serotype 2 antigen, the plates were used immediately after their sensitization according to the ELISA-3,3',5,5'-tetramethylbenzidine (TMBLue™) procedure. The control sera were distributed in the three plates. The positive control serum was used in 17 wells of each three plates and the negative control serum in 16 wells. Each of the six control serum fields was distributed in eight wells of each plate. The results are presented in Table 1.

TABLE 1

Reproducibility of antigen attachment between wells of a same plate or of different plates

| Serum | Plate #1 | | | Plate #2 | | | Plate #3 | | |
|---|---|---|---|---|---|---|---|---|---|
| | Mean | Standard deviation | Deviation % | Mean | Standard deviation | Deviation % | Mean | Standard deviation | Deviation % |
| B | 0.085 | 0.004 | 5 | 0.093 | 0.009 | 9 | 0.088 | 0.006 | 7 |
| CN | 0.022 | 0.008 | 34 | 0.019 | 0.010 | 51 | 0.025 | 0.009 | 38 |
| CP | 2.434 | 0.108 | 4 | 2.343 | 0.100 | 4 | 2.796 | 0.077 | 3 |
| EP1 | 1.867 | 0.138 | 7 | 1.802 | 0.149 | 8 | 2.439 | 0.094 | 6 |
| EP2 | 1.971 | 0.101 | 5 | 1.929 | 0.088 | 5 | 2.839 | 0.066 | 4 |
| EN1 | 0.028 | 0.007 | 24 | 0.025 | 0.010 | 41 | 0.031 | 0.005 | 18 |
| EN2 | 0.014 | 0.008 | 59 | 0.010 | 0.006 | 57 | 0.015 | 0.007 | 45 |
| ED1 | 0.614 | 0.039 | 6 | 0.688 | 0.040 | 6 | 0.945 | 0.049 | 5 |
| ED2 | 0.408 | 0.028 | 7 | 0.453 | 0.056 | 12 | 0.622 | 0.047 | 7 |

| Mean of the three plates | | |
|---|---|---|
| Mean | Standard deviation | Deviation % |
| 0.089 | 0.004 | 5 |
| 0.022 | 0.003 | 14 |
| 2.524 | 0.240 | 9 |
| 2.002 | 0.293 | 15 |
| 2.113 | 0.283 | 13 |
| 0.028 | 0.003 | 11 |
| 0.013 | 0.003 | 20 |
| 0.749 | 0.174 | 23 |
| 0.494 | 0.113 | 23 |

SPECIFICITY AND SENSITIVITY OF THE KIT

The specificity of the antigen was verified using sera from pigs experimentally infected with strains of *A. pleuropneumoniae* of different serotypes or with other types of bacteria. The ELISA method was used with ABTS as a chromogen.

The antigen gave positive reactions with sera from pigs experimentally infected with strains of *A. pieuropneumoniae* of serotype 2, and negative reactions with sera from pigs experimentally infected with strains of *A. pieuropneumoniae* of serotypes 1, 3, 4, 5, 7, 9, 10, 11 and 12 (Table 2). The sera from pigs inoculated with *H. parasuis, P. multocida, E. coli* or *A. suis* gave negative reactions.

TABLE 2

ELISA results of the antigen purified from
*A. pleurapneumoniae* serotype 2 against different sera
of pigs inoculated experimentally

| Sera from pigs inoculated with | No. of animals | Optical density |
|---|---|---|
| *A. pleuropneumoniae* serotype 1 (strain Shope 4074) | 18 | <0.05 |
| *A. pleuropneumoniae* serotype 2 (strain 4226) | 9 | 0.53 |
| *A. pleuropneumoniae* serotype 3 (strain 1421) | 6 | <0.05 |
| *A. pleuropneumoniae* serotype 4 (strain M62) | 3 | <0.05 |
| *A. pleuropneumoniae* serotype 5a (strain k17) | 6 | <0.05 |
| *A. pleuropneumoniae* serotype 5b (strain 81-750) | 28 | <0.05 |
| *A. pleuropneumoniae* serotype 7 (strain WF83) | 14 | <0.05 |
| *A. pleuropneumoniae* serotype 9 (strain CVJ 13261) | 2 | <0.05 |
| *A. pleuropneumoniae* serotype 10 (strain 13039) | 3 | <0.05 |
| *A. pleuropneumoniae* serotype 11 (strain 56153) | 2 | <0.05 |
| *A. pleuropneumoniae* serotype 12 (strain 2153-86) | 4 | <0.05 |
| *Actinobacillus suis* | 8 | <0.05 |
| *Haemophilus parasuis* | 10 | <0.05 |
| *Pasteurella multocida* | 9 | <0.05 |
| *Escherichia coli* | 5 | <0.05 |

Secondly, the plates were treated with HRP conjugate stabilizing solution after the sensitization with the antigen and the ELISA-3,3',5,5'-tetramethylbenzidine (TMBLue™) technique was used (Table 3).

TABLE 3

ELISA-TMBLue ™ responses of the antigen purified from
*A. pleuropneumoniae* serotype 2 against reference sera

| Serum used | Optical density | Visual Response |
|---|---|---|
| CN | 0.022 | 0 |
| CP | 2.524 | 4+ |
| EP1 | 2.002 | 4+ |
| EP2 | 2.113 | 4+ |
| EN1 | 0.028 | 0 |
| EN2 | 0.013 | 0 |
| ED1 | 0.749 | 1+ |
| ED2 | 0.494 | 1+ |

The CP, EP1 and EP2 sera gave positive responses. The CP serum came from a pool of sera obtained following the inoculation of two five weeks old piglets with the reference strain of *A. pleuropneumoniae*. The EP1 and EP2 sera were obtained from animals of a herd showing an acute infection and wherein mortality to *A. pleuropneumoniae* serotype 2 is frequently observed. The CN, EN1 and EN2 sera gave negative responses. The CN serum came from a pool of pig sera taken from a SPF (specific pathogen free) herd for which no history of pleuropneumonia, at the slaughter house, had been reported for at least four years. The EN1 and EN2 sera came from pigs from two herds with no history of pleuropneumonia and without lesions at the slaughter house. The ED1 and ED2 sera gave weak positive responses by ELISA. These sera were obtained from two pigs from a herd chronically infected with *A. pleuropneumoniae* serotype 2. These two sera are considered weak positives; they have indeed been classified by the service of pleuropneumonia of the Veterinary Medicine Faculty (VMF) of the University of Montreal as weakly positive sera by the ELISA reference test.

STUDY OF THE STABILITY OF THE KIT

During the preliminary trials, different techniques of antigen attachment, different buffers, as well as different methods of preservation of the plates were evaluated. The chosen method with respect to the antigen attachment consists in diluting 1.5 ml of antigen in 73.5 ml of PBS-EDTA buffer, pH 7.3. 100 µl of this solution is then distributed in each well of the 96-well plates (Nunc™), and the plates are incubated 18 hours at 4° C. The content of the plates is emptied and 100 µl of HRP conjugate stabilizing solution is added to each well. The plates are kept at 4° C. The stability of the plates is assessed monthly. In addition to the three controls included in the kit, eight additional sera are used for the stability study. These sera are kept at –20° C. and a new aliquot is used for each assay. The kit is validated as described in the protocol of utilization. As shown in Table 4, the kit is stable for at least 6 months.

TABLE 4

Stability assessment of the visual test kit for
*A. pleuropneumoniae* serotype 2

| | Number of weeks at 4° C. | |
|---|---|---|
| Sera | 0 | 2 |
| Positives (4+, 3+, 2+) | 4* | 4 |
| Negatives (0+) | 2 | 2 |

*Number of sera

REPRODUCIBILITY OF THE KIT DEPENDING ON THE USER

One lot of three complete kits were prepared. Six (6) different sera were obtained from the serology laboratory of the VMF; one kit as well as one aliquot of each undiluted serum was given to three different users. Identical results were obtained by the three different users (Table 5).

TABLE 5

Evaluation of the visual test kit for
*A. pleuropneumoniae* serotype 2 by three different users

| | batch | | |
|---|---|---|---|
| Sera | User #1 | User #2 | User #3 |
| Positives (4+, 3+, 2+) | 2* | 2 | 2 |
| Weak positives (1+) | 2 | 2 | 2 |
| Negatives (0+) | 2 | 2 | 2 |

*Number of sera

Finally in order to verify the sensitivity and the specificity of the kit of the present invention, several complete kits were prepared. A total of 259 sera were obtained from the pleuropneumonia serology laboratory of the Veterinary Medicine Faculty of the University of Montreal These sera had been classified by this laboratory and had been obtained from herds having a well known sanitary status. The 117 sera classified as negative by the pleuropneumonia serology laboratory were confirmed as negative with the kit of the present invention. Within the 142 sera classified as positive by the pleuropneumonia serology laboratory, 2 sera gave a 1+ response with the kit of the present invention and the remaining 140 sera gave a 2–4+ response therewith (Table 6).

TABLE 6

Sensitivity and specificity of the visual test kit for
*A. pleuropneumoniae* serotype 2

| Results with the kit | Results with the "golden test" | |
|---|---|---|
| | Positive | Negative |
| 4–3+ | 108 | 0 |
| 2+ | 32 | 0 |
| 1+ | 2 | |
| 0 | 0 | 117 |
| total: | 142 | 117 = 259 |

DISCUSSION

The determination of the sensitivity and the specificity of a test is carried out either by using animal populations having a status which is clearly identified as "infected" or as "healthy" or by comparing the results of the test with a reference test, a "golden test". In accordance with the present invention, both methods were used.

A sera of well defined status, 85 sera from pigs infected experimentally with strains of *A. pleuropneumoniae* of different serotypes or with different bacteria were used. Thereafter, eight additional sera of pigs of well defined status were used; one serum came from a pig infected experimentally with *A. pleuropneumoniae* serotype 2 (strain ATCC 27089), one serum came from a pool of sera of specific pathogen free pigs (SPF) and six pig sera came from pigs belonging to different herds having a well defined status.

The ELISA kit of the present invention gave a positive response only with sera from pigs infected experimentally or naturally with *A. pleuropneumoniae* serotype 2. The sera of pigs infected experimentally with strains of *A. pleuropneumoniae* serotypes 1, 2, 3, 5, 9, 10, 11 and 12 and 11; *H. parasuis*, *P. multocida*, *E. coli* or *A. suis*, as well as the two pools of sera from SPF pigs gave negative responses. The ED1 and ED2 sera came from pigs having no clinical sign of pleuropneumonia but evidence of infection with *A. pleuropneumoniae* serotype 2 had been observed in the herd. These sera were thus considered as weakly positive.

The ELISA kit of the present invention is stable at 4° C. for at least 6 months. The stability studies are still in progress.

The specificity and sensitivity of the kit of the present invention was also evaluated using 259 pig sera. These sera were furnished by the pleuropneumonia laboratory of the Veterinary Medicine Faculty of the University of Montreal. This laboratory was considered as the laboratory of reference with respect to the serology of *Actinobacillus pleuropneumoniae* and the results obtained by this laboratory were considered as the "golden test". This laboratory has been analyzing between 30,000 and 40,000 pig sera per year for more than 10 years. The methodology used by the pleuropneumonia laboratory consists in an ELISA technique standardized in order to determine the presence of antibodies. A complement fixation test is no longer in use in this laboratory, due to its lack of sensitivity and specificity. The serology laboratory has developed its standardized ELISA test by comparing different types of antigen (Gottschalk, M. et al., 1994, *Vet. Microbiol.*, 42:91–104). In view of the great numbers of sera received by this laboratory, the results obtained thereby were considered as a reference. The status of the sera as obtained by this laboratory, whether positive or negative, was thus well certified. A correlation tion of 100% was observed between the results obtained with the kit of the present invention and the classification form the serology laboratory. All the sera classified as negative by the reference serology laboratory were thus determined as negative by the kit of the present invention. If one considers the weak positives or positives 1+as positives, all the sera classified as positive by the reference laboratory gave a positive response using the kit of the present invention.

The kit of the present invention differs from the ELISA method used by the reference serology laboratory. In the method used by the latter, the antigen is fixed to the plates in a PBS buffer and the plates are used immediately following the antigen fixation. In addition, the serology laboratory utilizes a computerized reading protocol for the determination of the antibodies in the samples (Trottier, Y. L. et al., 1992, *J. Clin. Microbiol.*, 30:46–53).

In the case of the kit of the present invention, the antigen is purified using an antigen retained in the phenol fraction (not in the water fraction) and the antigen fixation is different. Indeed, the purified antigen is resuspended in a PBS-EDTA buffer which is then added to the wells of the plates.

After an 18 hour incubation, HRP conjugate stabilizing solution is added to each well. The antibodies in the samples are then determined visually by a chromogen, preferably 3,3',5,5'-tetramethylbenzidine (TMBLue™).

When compared to the standardized ELISA method used by the serology laboratory, the kit of the present invention, demonstrates a sensitivity and a specificity of 100%. In addition, The kit of the present invention is faster to use than the ELISA-ABTS (2,2'-azino-bis(3-ethylbenzthiazoline)-6-sulfonic acid)method of the prior art. Indeed, using the kit of the present invention, results are obtained in less than one hour while a minimum of three hours are required for the ELISA-ABTS method in addition to the overnight step required for the fixation of the antigen. Furthermore, ABTS is considered as potentially carcinogenic in addition to being only moderately stable.

The kit of the present invention is easily used and provides rapid results. The kit can be used by a veterinarian having a minimum of experience, it may be used in the field where the animals are kept and does not require laboratory skills, since only simple steps need to be performed. In addition, this kit was demonstrated to give highly reliable and reproducible results independently of the user. The results obtained with the kit of the present invention are identical to those obtained by the pleuropneumonia laboratory of the VMF. The kit of the present invention is thus highly advantageous as compared to the presently available laboratory tests with respect to its rapidity, reliability, sensitivity, specificity, stability and cost.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

TESTING ALTERNATIVE OPTIONS FOR STABILIZING THE ANTIGEN

That the following different options were tested to stabilize the antigen coated to the plates in accordance with the present invention.

a) Antigen Without any Agent for the Stabilization
Sensitization of the Plates:
   Dilute the antigen in PBS-EDTA buffer, pH 7.3 to reach the appropriate concentration.
   Add 100 µl of antigen to each well.
   Seal the plate with an acetate sheet.
   Incubate overnight at 4° C.
Results:
Plates kept at 22° C. and 37° C.:
   The reaction disappeared after 1–2 days.
Plates kept at 4° C.:
   The reaction is significantly weaker after 14 days
b) Antigen Stabilized with SPGA (added concurrently with coating of the antigen)
Sensitization of the plates:
   Dilute the antigen in SPGA buffer, pH 7.3 to reach the appropriate concentration. Mixtures of PBS-EDTA with SPGA (1:1, 1:0.5 and 1:0.25) were also tested.
   Add 100 µl of antigen to each well.
   Seal the plate with an acetate sheet.
   Incubate overnight at 4° C.

| SPGA: |
| --- |
| 0.218 M sucrose |
| 0.0038 M monopotassium phosphate |
| 0.0049 M monosodium glutamate |
| 1% BSA (bovine serum albumin) |

Results:
   The SPGA competes with the antigen, thus NO positive reaction was obtained.
c) Antigen Stabilized with SPGA (added 24 hours after coating with the antigen)
Sensitization of the plates:
   Dilute the antigen in PBS-EDTA buffer, pH 7.3 to reach the appropriate concentration.
   Add 100 µl of antigen to each well.
   Seal the plate with an acetate sheet.
   Incubate overnight at 4° C.
   The content of the wells are emptied and 100 µl of SPGA is added to each well.
SPGA: same as for b) above
Results:
   The positive reaction dropped in plates kept at any temperature after 7 days. Non-specific background is very high.
d) Antigen Fixed under Vacuum
Sensitization of the Plates:
   Dilute the antigen in PBS-EDTA buffer, pH 7.3 to reach the appropriate concentration.
   Add 100 µl of antigen to each well.
   Seal the plate with an acetate sheet.
   Incubate overnight at 4° C.
   A complete vacuum of the plate is carried out.
Results:
   The positive results are weaker at day 12 in plates kept at 4° C. High variability intra-plate (between wells). Low repeatability.
e) Antigen Fixed in Nitrogen
Sensitization of the Plates:
   Dilute the antigen in PBS-EDTA buffer, pH 7.3 to reach the appropriate concentration.
   Add 100 µl of antigen to each well.
   Seal the plate with an acetate sheet.
   Incubate overnight at 4° C.
   A vacuum of the plate is carried out.
   The atmosphere is replaced by nitrogen.
Results:
   Similar results to those obtained in d) above.
f) Antigen Fixed by Lyophilization
Sensitization of the plates:
   Dilute the antigen in PBS-EDTA buffer, pH 7.3 to reach the appropriate concentration.
   Add 100 µl of antigen to each well.
   Seal the plate with an acetate sheet.
   Incubate overnight at 4° C.
   The antigen is lyophilized directly on the plate.
Results:
   The positive results are weaker at day 12 in plates kept at 4° C.
   Similar results to those obtained in d) and e) above.
g) Plates kept at −20° C.
Sensitization of the Plates:
   Dilute the antigen in PBS-EDTA buffer, pH 7.3 to reach the appropriate concentration.
   Add 100 µl of antigen to each well.
   Seal the plate with an acetate sheet.
   Incubate overnight at 4° C.
   The plates are kept at −20° C.
Results:
   The positive reaction is weaker after 14 days. High variability among different wells.
h) HRP Stabilization Reactive (added concurrently with the coating of the antigen)
Sensitization of the plates:
   Dilute the antigen in HRP conjugate stabilizing solution to reach the appropriate concentration.
   Add 100 µl of antigen to each well.
   Seal the plate with an acetate sheet.
   Incubate overnight at 4° C.
Results:
   The HRP stabilization reactive competes with the antigen, thus NO positive reaction was obtained.
i) HRP Stabilization Reactive (added 24 hours after coating with the antigen)
Sensitization of the plates:
   Dilute the antigen in PBS-EDTA buffer, pH 7.3 to reach the appropriate concentration.
   Add 100 µl of antigen to each well.
   Seal the plate with an acetate sheet.
   Incubate overnight at 4° C.
   The content of the wells are emptied and 100 µl of HRP conjugate stabilizing solution is added to each well.
Results:
   The plates keep the active antigen and good reproducibility at different temperatures (4° C., 22° C. and 37° C.).
   At 4° C., plates can be kept for at least 9 months without any change in optical densities obtained by ELISA. This was the procedure chosen to prepare the plates of the present invention.

We claim:
1. An enzyme-linked immunosorbent assay (ELISA) diagnostic kit for the assay of *A. pleuropneumoniae* serotype 2 antibody in the serum of pig comprising in separate packaging:
   a) a solid support having bound thereto a purified lipopolysaccharide *A. pleuropneumoniae* serotype 2 antigen for a specific binding to anti-*A pleuropneumoniae* serotype 2 antibodies present in the serum of the pig, said bound antigen being stabilized with phosphate buffered saline pH 7.2, containing bovine serum albumin (BSA), 0. 1% thimerosal and caprylic acid until use; and  a detectably labeled conjugate which binds to pigs antibodies bound to the solid support of a).

2. The kit of claim 1, wherein the bound antigen of a) is stable for at least nine months at 4° C.

3. The kit of claim 1, which further comprises c) a substrate which allows the visualization of the detectably labeled conjugate.

4. The kit of claim 3, wherein said detectably labeled conjugate comprises an enzyme label.

5. The kit of claim 4, wherein said substrate is a composition for providing a calorimetric, fluorimetric or chemiluminescent signal in the presence of said enzyme label.

6. The kit of claim 4, wherein said detectably labeled conjugate comprises pig anti-IgG immunoglobulins coupled to peroxidase.

7. The kit of claim 5, wherein said calorimetric composition is 3,3',5,5'-tetramethylbenzidine.

8. The kit of claim 7 which contains the serum that serves as the positive control in a lyophilized form.

9. The kit of claim 8 wherein the serum is in the amount of about 0.4 ml of lyophilized serum.

10. The kit of claim 1, wherein said solid support is a 96-well plate.

11. An enzyme-linked immunosorbent assay (ELISA) diagnostic kit for the assay of *A. pleuropneumoniae* serotype 2 antibody in the serum of pig comprising in separate packaging;

a) a solid support having bound thereto a purified lipopolysaccharide *A. pleuropneumaniae* serotype 2 antigen for a specific binding to anti-*A pleuropneumaniae* serotype 2 antibodies present in the serum of the pig, said bound antigen being stabilized with phosphate buffered saline pH 7.2, containing BSA, 0.1% thimerosal and caprylic acid until use;

b) a positive control vial of serum from pigs experimentally inoculated with a strain of *A. pleuropneumoniae* serotype 2;

c) a negative control vial of pig serum from a *A. pleuropneumoniae* free herd;

a conjugate vial of pig anti-IgG immunoglobulins coupled to peroxidase; and e) a colorimetric composition consisting of 3,3',5,5'-tetramethylbenzidine or 2,2'-azino-bis(3-ethylbenzthia-zoline-6-sulfonic acid).

12. The kit of claim 11, wherein the bound antigen of a) is stable for at least nine months at 4° C.

13. A method for the preparation of the kit of claim 1, which comprises the steps of:

a) purifying lipopolysaccharide *A. pleuropneumoniae* serotype 2 antigen by phenol extraction and centrifugation of said antigen bacterial crude extract;

b) fixing the antigen of step a) to a solid support and stabilizing said fixed antigen;

c) immunizing animals with a strain of *A. pleuropneumoniae* serotype 2 and collecting serum to serve as positive control sera; and d) collecting sera from *A. pleuropneumoniae* free herds to serve as negative control sera.

14. The kit of claim 13, wherein the fixing of the antigen of step b) is effected by storing it in a solution comprising phosphate buffered saline pH 7.2 containing bovine serum albumin (BSA), 0. 1% thimerosal and caprylic acid, which keeps said bound antigen of step b) stable for at least nine months at 4° C.

15. The kit of claim 1 further comprising at least one of the following:

c) serum from pigs experimentally inoculated with a strain of *A pleuropneumoniae* serotype 2 to serve as a positive control; and d) pig serum from a specific pathogen free herd to serve as a negative control.

16. The kit of claim 15 which contains the serum that serves as the negative control in a lyophilized form.

17. The kit of claim 16 wherein the serum is in the amount of about 0.4 ml of lyophilized serum.

18. A solid support for use in an assay of *A pleuropneumoniae* serotype 2 antibodies in the serum of pigs having bound thereto a purified lipopolysaccharide *A pleuropneumoniae* serotype 2 unreacted antigen for a specific binding to anti-*A pleuropneumoniae* serotype 2 antibodies present in the serum of pigs, wherein the bound antigen is stored in phosphate buffered saline pH 7.2, containing BSA, 0.1% thimerosal and caprylic acid until use.

19. The solid support of claim 18 that is a 96-well plate.

* * * * *